United States Patent [19]
Burroughs et al.

[11] Patent Number: 5,938,642
[45] Date of Patent: Aug. 17, 1999

[54] MULTIPLE DOSE MEDICATION DISPENSING DEVICE

[75] Inventors: Andrew Burroughs, Kenosha, Wis.; Dave Hixson; Andrew Hodge, both of Evanston, Ill.

[73] Assignee: Eli Lilly and Company, Indianapolis, Ind.

[21] Appl. No.: 09/012,533

[22] Filed: Jan. 23, 1998

Related U.S. Application Data

[63] Continuation of application No. 08/399,764, Mar. 7, 1995, abandoned.

[51] Int. Cl.⁶ .................................................. A61M 5/00
[52] U.S. Cl. .......................... 604/208; 604/218; 604/232
[58] Field of Search .................................. 604/207, 208, 604/209, 211, 186, 232, 227, 246, 218, 181, 187; 222/309

[56] References Cited

U.S. PATENT DOCUMENTS

| | | | |
|---|---|---|---|
| 4,413,760 | 11/1983 | Paton | 222/309 |
| 4,592,745 | 6/1986 | Rex et al. | 604/211 |
| 4,865,591 | 9/1989 | Sams | 604/186 |
| 4,883,472 | 11/1989 | Michel | 604/208 |
| 4,936,833 | 6/1990 | Sams . | |
| 4,973,318 | 11/1990 | Holm . | |
| 5,017,190 | 5/1991 | Simon et al. | 604/207 |
| 5,042,977 | 8/1991 | Bechtold et al. | 604/134 |
| 5,085,641 | 2/1992 | Snarnoff | 604/134 |
| 5,092,842 | 3/1992 | Bechtold et al. | 604/135 |
| 5,104,380 | 4/1992 | Holman et al. | 604/117 |
| 5,112,317 | 5/1992 | Michel | 604/208 |
| 5,114,406 | 5/1992 | Gabriel et al. | 604/136 |
| 5,232,459 | 8/1993 | Hjertman | 604/208 |
| 5,244,465 | 9/1993 | Michel | 604/208 |
| 5,279,585 | 1/1994 | Balkwill | 604/207 |
| 5,279,586 | 1/1994 | Balkwill | 604/207 |
| 5,295,976 | 3/1994 | Harris | 604/211 |
| 5,304,152 | 4/1994 | Sams | 604/207 |
| 5,308,340 | 5/1994 | Harris | 604/208 |
| 5,328,486 | 7/1994 | Woodruff | 604/207 |
| 5,383,865 | 1/1995 | Michel | 604/232 |
| 5,391,157 | 2/1995 | Harris et al. | 604/208 |
| 5,480,387 | 1/1996 | Gabriel et al. | 604/134 |
| 5,591,136 | 1/1997 | Gabriel . | |

FOREIGN PATENT DOCUMENTS

| | | |
|---|---|---|
| 0 498 737 | 8/1992 | European Pat. Off. . |
| WO92/18179 | 10/1992 | WIPO . |
| 9 307 922 | 4/1993 | WIPO . |
| WO 93/07922 | 4/1993 | WIPO . |

Primary Examiner—Ronald Stright
Attorney, Agent, or Firm—Baker & Daniels

[57] ABSTRACT

A multi-use pen-shaped medication dispensing device made of a plastic material that is recyclable after the contents of the medication cartridge have been exhausted. The device is made of a minimal number of parts, which include a housing, a dial assembly, a generally cylindrical button assembly located within the proximal end of the dial assembly, an internally threaded nut, and an externally threaded leadscrew. The device is arranged so that the dial must be rotated to the zero dose position prior to setting a dose. The device includes a lockout mechanism that prevents the dial from being depressed during dosing. The device further includes a mechanism that limits the maximum dosage that can be dialed up and a mechanism that prevents the user from dialing up a dosage greater than that remaining in the cartridge.

17 Claims, 17 Drawing Sheets

FIG_5

FIG_6

FIG_8

FIG_10

FIG_11

FIG_12

FIG_13

FIG._15

FIG_16

MULTIPLE DOSE MEDICATION DISPENSING DEVICE

This is a continuation of application Ser. No. 08/399,764, filed Mar. 7, 1995, now abandoned, the disclosure of which is expressly incorporated herein by reference.

BACKGROUND OF THE INVENTION

The present invention relates generally to medical dispensing devices and, more particularly, to a recyclable dispensing device that permits selectively measured dosages of a liquid to be dispensed.

Patients suffering from diseases such as diabetes must inject themselves several times each day with an insulin solution. Since the volume of insulin solution to be injected varies from injection to injection, it is necessary for such patients to be able to measure a precise volume of insulin. Diabetics have conventionally used a syringe for injection of insulin. However, it is difficult to control the operation of the syringe as well as the quantity of drug injected.

In order to permit a diabetic to measure and administer a more accurate and controlled dosage, injector pens have been developed which enable a particular dosage to be accurately and conveniently measured. Generally, these pens are secured onto a cartridge having a particular quantity of liquid medication sealed therein. The cartridge includes a plunger and a mechanism for advancing the plunger in the cartridge in such a manner to dispense the medication. Injector pens may be reusable or disposable. In reusable pens, a user can change a spent cartridge and reset the leadscrew of the pen back to its initial position. In a disposable pen, the cartridge is permanently captured in the pen which is disposed of after the contents of the cartridge have been exhausted.

One such disposable pen that has functioned very adequately is disclosed in U.S. Pat. No. 5,295,976. Specifically, a dispensing device is disclosed and includes an internally threaded collar and an externally threaded plunger rod. In order to set a dosage of medication to be delivered, the collar is rotated thereby causing displacement of the collar toward the proximal end of the injection device. Rotation of the collar causes the integral cap to become effectively displaced both rotationally and axially toward the proximal end of the pen. As this displacement occurs, the segment of the dose-indicating scale which is visible through a window varies showing a linear increase in the number to indicate an increase dosage of liquid to be dispensed. Once the desired dosage is selected, a force is applied to the end of the cap causing a linear displacement of the cap, integral plunger rod, and piston to dispense liquid from the container. The dispensing displacement of the plunger rod is halted by abutting contact between the cap and a stop element.

In U.S. Pat. No. 5,308,340, another recyclable injection device is disclosed. In particular, a plunger rod is received within the housing for exerting a force on a piston closing a second end of the container. The plunger rod has a noncylindrical cross section with a first surface including threads and a second surface which can, optionally, include a series of ratchet teeth. A collar is received within the housing adjacent the second end of the container for permanently retaining the container of liquid within the housing. The plunger rod passes through the noncylindrical opening in the collar and is prevented from rotating with respect to the housing by the collar. A hollow cap envelopes the plunger rod opposite the container of liquid. The skirt of the hollow cap extends inside the housing. The cap includes a threaded interior surface which movably engages the plunger rod for calibrated adjustment relative thereto. A stop is provided within the housing, and a distal facing surface is provided on the hollow cap for contacting the stop upon linear movement of the cap and plunger rod as a unit toward the container to dispense liquid therefrom. In operation, the cap is rotated in a counterclockwise direction causing the threads of the cap to travel along the threaded portion of the rod. This rotation does not cause displacement of the plunger rod with respect to the housing, but backs the distal end of the proximal cap portion away from a stop shoulder on the inside of the housing. When the cap has been positioned to the desired dosage, pressure is applied to the end of the cap for causing it to move linearly toward the distal end of the housing until a shoulder defined by a radially exposed portion of the distal end contacts a stop.

SUMMARY OF THE INVENTION

The present invention provides a medication injection device comprising a housing, a dose setting mechanism within the housing, and a delivery mechanism within the housing for advancing a leadscrew. A liquid medication product is housed in a variable volume cartridge within the housing of the device. Upon actuation of the delivery mechanism, the leadscrew is advanced against a movable piston in the cartridge to advance the piston thereby causing a preset quantity of medication to be delivered out of the needle of the device.

In one embodiment, the device is made entirely out of a recyclable plastic material, except for the glass container, steel needle and label. The dose setting mechanism comprises a dial assembly including a clutching device for engaging and disengaging a generally cylindrical internally threaded nut, which is threaded onto an externally threaded leadscrew. A dose is set by rotating the nut with respect to the leadscrew. The nut is rotated by rotating the dial. However, the nut must be engaged with the dial so that rotating the dial also rotates the nut. The clutching device comprises a series of splines on the inner cylindrical surface of the dial which axially engage corresponding splines on the outer surface of the nut. The splines are engaged with one another by retracting the dial with respect to the nut after the dial has been rotated to its zero dose position.

The dial assembly includes a mechanism that prevents the user from retracting the dial prior to rotating the dial to its zero dose position. This mechanism comprises a finger formed in the housing that rides within a groove formed at the distal end of the dial assembly as the dial assembly is rotated. The dial cannot be pulled out in any radial position other than the zero dose radial position due to the interference formed between the finger and the walls of the groove. In the zero dose position, the housing finger rides up within a spline that extends axially uninterrupted to enable the dial to be proximally retracted with respect to the housing only when the dial is in its zero dose radial position.

The device includes a mechanism that limits the maximum dosage that can be set. This mechanism comprises a helical groove formed in the housing and a pair of flexible fingers formed in the dial assembly. Upon rotating the dial to set a dose, the dial is retracted with respect to the housing because the dial fingers ride up the internal housing groove. Once the dial fingers reach the proximal end of the housing groove, further rotation of the dial is prohibited, thereby indicating to the user that the maximum dosage has been dialed.

The device further includes a mechanism for automatically locking out the dial from an inadvertent injection after the dial has been retracted to set a dosage. This lockout mechanism comprises the above-mentioned fingers in the dial assembly that fall into the helical groove in the housing upon retracting the dial with respect to the housing. The interference fit formed by the fingers in the groove prevents forward movement of the dial in the event of inadvertent pressure being applied to the end of the dial. The lockout mechanism is released by a button assembly that is disposed within the proximal end of the dial assembly. The button assembly is sized and configured so that it must be depressed upon initiating an injection. Upon depressing the button assembly, it bottoms out against the dial, whereupon the dial moves forwardly so that the flexible fingers move past the groove in the housing.

One of the two flexible fingers of the dial assembly has an extension which, when the button is pressed, is pushed radially out. This finger falls within a separate groove in the housing as the "end-of-dose" stop surface of the dial engages the corresponding stop surface on the housing, thereby producing an audible "click" indicating that the entire dosage has been injected. The housing further includes radially inwardly extending tangs at the proximal end thereof which engage ratchet teeth in the leadscrew to prevent the leadscrew from backing up in the proximal direction. These tangs are in constant engagement with the leadscrew, thereby preventing the leadscrew from rotating upon rotation of the nut.

The device also includes a mechanism which indicates to the user that there is an insufficient dosage remaining in the container of medication. This mechanism prevents the user from setting a dosage greater than that available to be delivered. The insufficient dose remaining feature comprises a 350° helical thread on the inner cylindrical surface of the nut and a raised finger forward at the end of the leadscrew where the external thread terminates. As the nut rotates about the leadscrew, the ledge formed by the termination of the helical thread on the nut engages the finger, thereby positively preventing further rotation of the nut in that direction.

An advantage of the medication dispensing device of the present invention is that the dosing function is locked out until the dial has been rotated to its zero dose position, thereby ensuring an accurate dosage.

Another advantage of the present invention is that the device is an inexpensive recyclable pen that is designed to allow a user to dose in single unit increments, which are each displayed in a single unit display.

Another advantage of the present invention is that the end-of-dose click arrangement is adjacent the end-of-dose stop to provide increased accuracy of an end of dose.

Another advantage of the present invention is that the device includes a dosage lockout mechanism that prevents an inadvertent delivery of a dosage of medication.

A further advantage of the present invention is that the insufficient remaining dose mechanism comprises a radial stop which ensures that the user cannot dial up a dosage greater than that remaining in the cartridge.

Yet another advantage of the present invention is that the device is made of inexpensive materials and is nearly 100% recyclable after the contents of the cartridge have been depleted.

The present invention, in one form thereof, comprises an apparatus for effecting delivery of an injectable product. The apparatus comprises a housing and a container secured to the housing and including a piston, an exit, and an injectable product between the piston and the exit. A drive stem is disposed in the housing and is in engagement with the piston. The length of axial movement of the drive stem with respect to the housing between a pre-injection position and a post-injection position defines the stroke length of the drive stem. A manually adjustable dosage metering mechanism is disposed in the housing and is movable between a zero dose position, wherein the stroke length is zero, and a second dose position for enabling a user to selectively adjust the stroke length of the drive stem. The apparatus further includes means coupled to the dosage metering mechanism for preventing the stroke length of the drive stem from being adjusted until the dosage metering mechanism has been set to the zero dose position.

In another form of the present invention, the apparatus includes a drive assembly mounted to the housing and manually advanceable in the housing between a dose setting position and an injection position for manually moving the drive stem to drive the piston within a container. The drive assembly is locked from movement with respect to the housing along the axis of ejection while in the dose setting position. A disengaging device is secured to at least one of the drive assembly and the housing to unlock the drive assembly from the housing to enable the drive assembly to be axially advanceable with respect to the housing to move the drive assembly from the dose setting position to the injection position.

The present invention further includes a method of delivering a selected dosage of injectable product. The method includes the step of rotating a knob extending from an injector housing to establish a zero dose rotational position of the knob, wherein rotation of the knob causes rotation of the dial assembly attached to the knob. The knob and dial assembly are retracted while in the zero dose position to cause the dial assembly to engage an internally threaded nut with the housing. The knob is then rotated to cause rotation of the dial and the nut which causes axial translation of the dial and the nut, thereby setting a desired dosage of injectable product to be delivered. The knob is then manually depressed to depress the dial assembly and the nut and drive stem to cause the drive stem to advance the piston within the container of injectable product, thereby forcing a set dosage of injectable product to be delivered out of the exit of the container. The step of depressing the knob causes the dial assembly to become disengaged from the nut so that the knob may be rotated independently of the nut after delivery of the set dosage of injectable product has been completed.

DESCRIPTION OF THE PREFERRED EMBODIMENT

For purposes of this application, the term "proximal" shall designate a relative axial position toward the knob end of the delivery mechanism, and the term "distal" shall designate a relative axial position toward the delivery needle end of the delivery mechanism.

Figure 1:
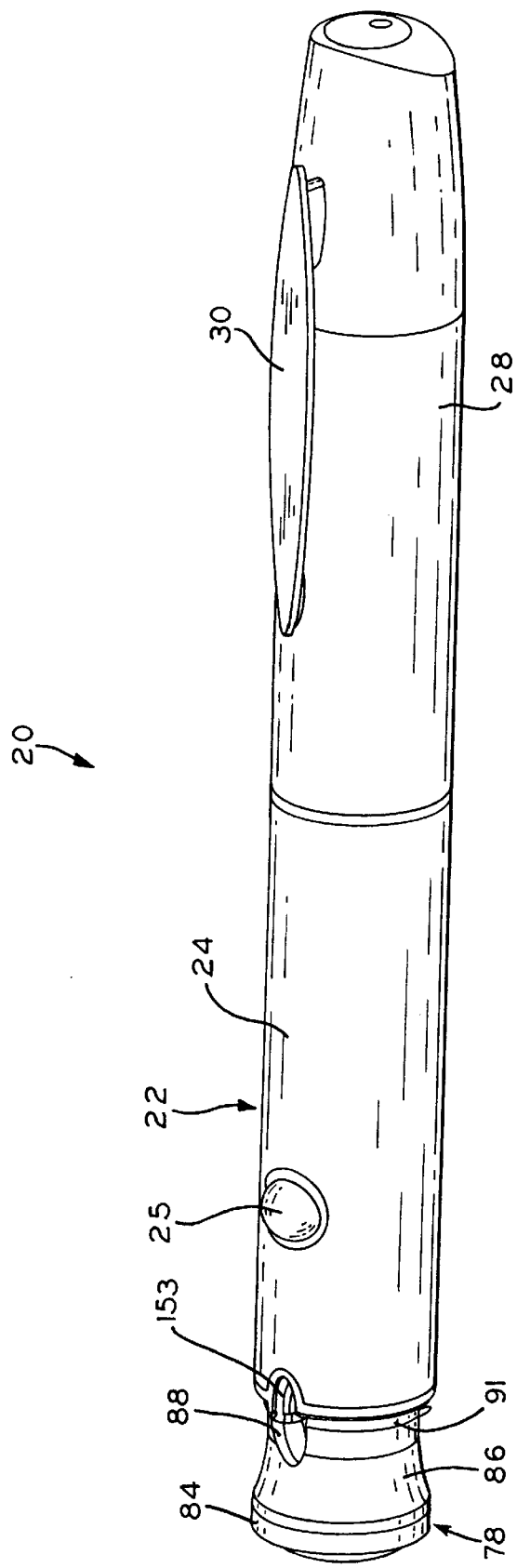
FIG. 1 is a perspective view of one embodiment of a medication dispensing device in accordance with the present invention.
Figure 2:
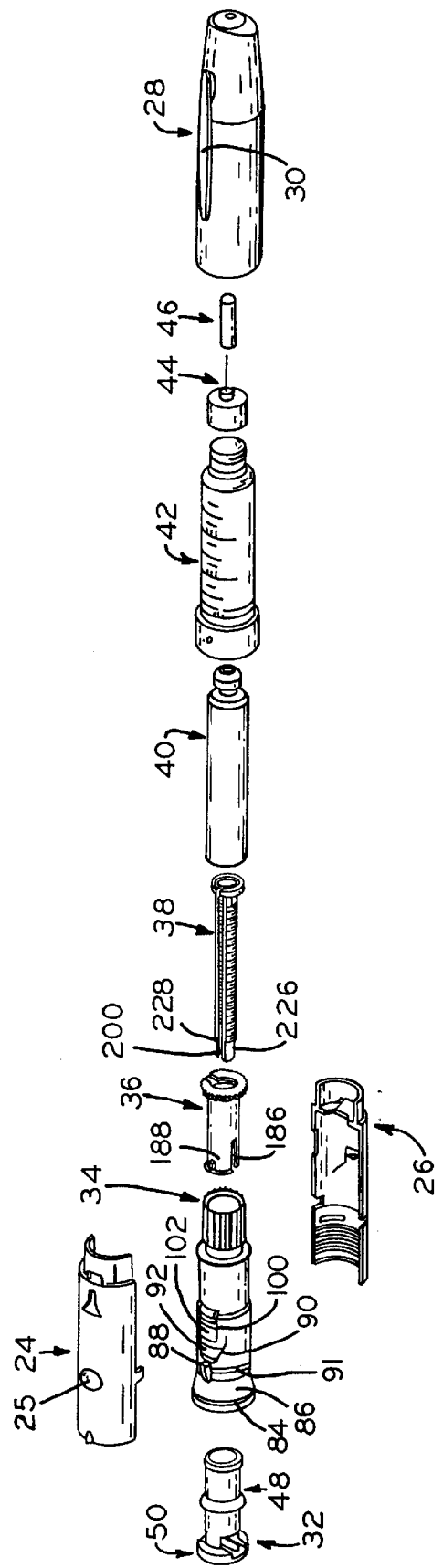
FIG. 2 is an exploded view of the device of FIG. 1.

Referring to FIGS. 1 and 2, there is shown an injection medication device 20 having the general appearance of a pen or mechanical pencil. The device comprises a mechanism housing 22 having a first part 24 and a second part 26 (FIG. 2). Housing parts 24 and 26 are secured together in a suitable fashion, e.g. chemical bonding with a suitable adhesive or a solvent. A cap 28 is snapped onto the distal end of mechanism housing 22. Cap 28 includes a clip 30 which cooperates with the side wall of cap 28 to provide a convenient means for holding the pen device 20 in a shirt pocket. Referring to FIG. 2, the major components of medication device 20 include disengaging device 32, a dial assembly 34, a nut 36, and a drive stem 38. Together, dial assembly 34 and nut 36 form both a dosage metering mechanism and a drive assembly. A cartridge 40 is inserted into a distal body 42 to which is attached a needle assembly 44 and needle cover 46. All of the components of medication device 20, except cartridge 40 and needle 44 may be made of a plastic material that is suitable for recycling. Suitable plastics are high flow polycarbonates resins which can be processed by conventional injection molding and extrusion. In one embodiment, the housing parts 24, 26 and distal body 42 are made from an optically clear polycarbonate material, and the remaining plastic components are made from ABS resins. These plastics are recyclable, thereby making disposal of the device environmentally desirable.

Figure 3:
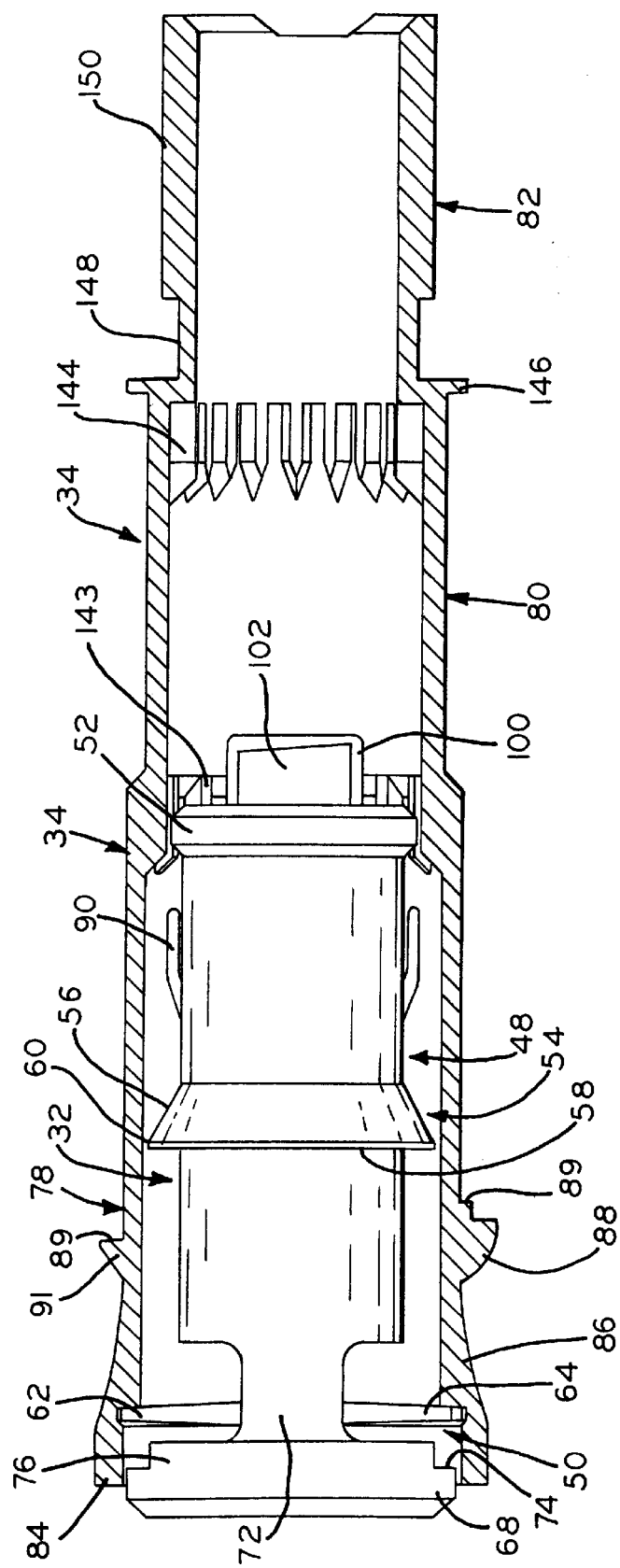
FIG. 3 is an enlarged longitudinal sectional view of a portion of the medication dispensing device of FIG. 1, particularly showing the button assembly disposed within dial assembly.
Figure 4:
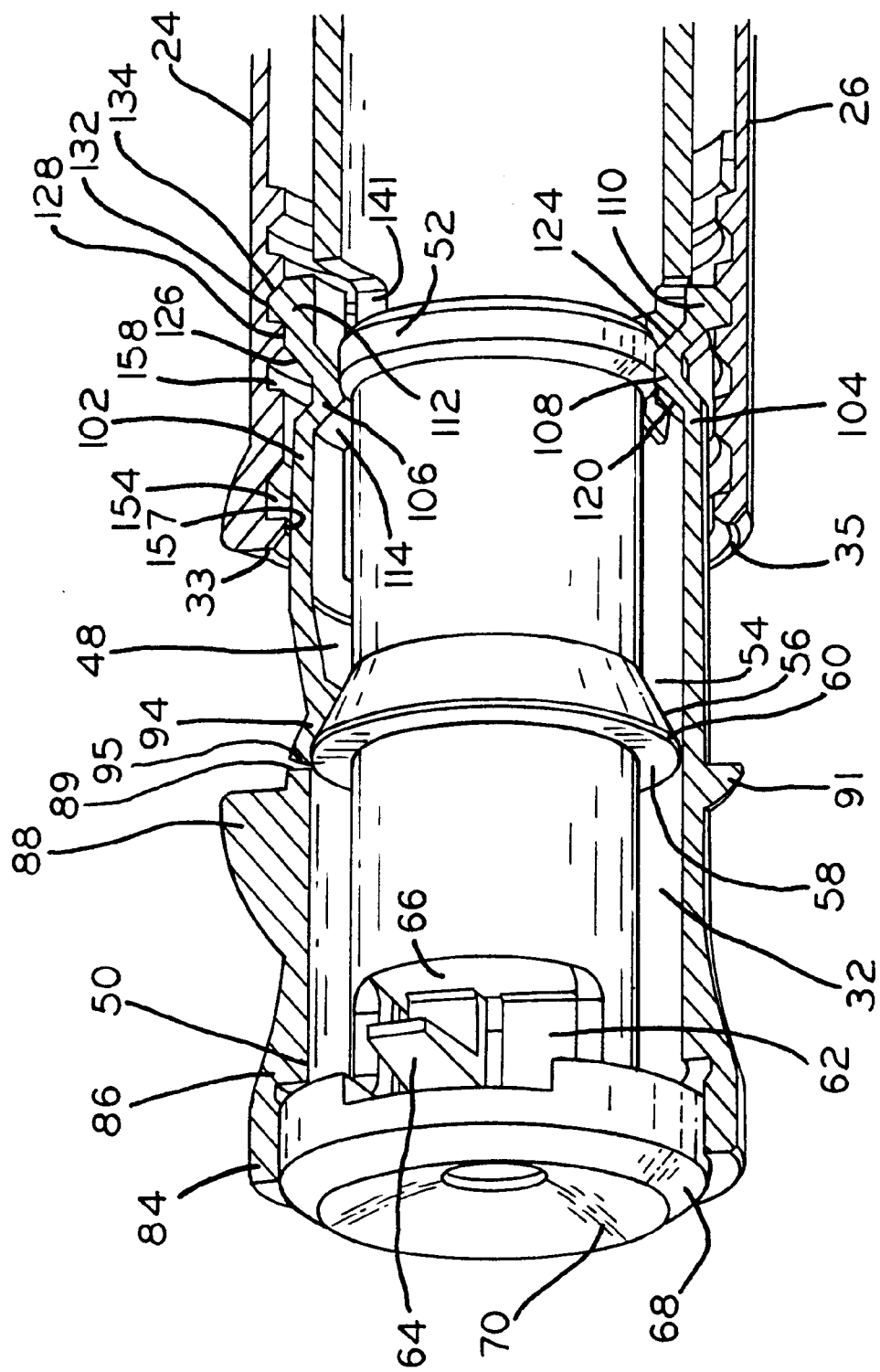
FIG. 4 is an enlarged perspective view, in partial section, of the medication dispensing device of FIG. 1, particularly showing the button assembly disposed in the dial assembly.

Referring to FIG. 4, disengaging device 32 comprises a hollow cylindrical portion 48 having a proximal end 50. Cylindrical portion 48 includes a distal end 52 in the form of an annular bead and further includes an enlarged diameter ring 54 comprising a tapered surface 56 and an enlarged diameter flat surface 58. The inner section of surfaces 56 and 58 forms an enlarged diameter shoulder surface 60. The proximal end 50 of button assembly 32 comprises two flexible fingers 62, 64, each extending from a base surface 66. As shown in FIG. 4, each finger 62, 64 is L-shaped and includes a first leg which extends from base surface 66 and is parallel with the axis of medical device 20, and a second leg extending radially about 90° from the first leg. Proximal end 50 of disengaging device 32 further includes a finger-engageable end 68 having a recessed surface 70. End 68 is integrally connected to hollow cylindrical portion 48 by connection portions 72 (FIG. 3). Proximal end 50 includes a surface 74 (FIG. 3) that is formed from reduced length portion 76.

Figure 10:
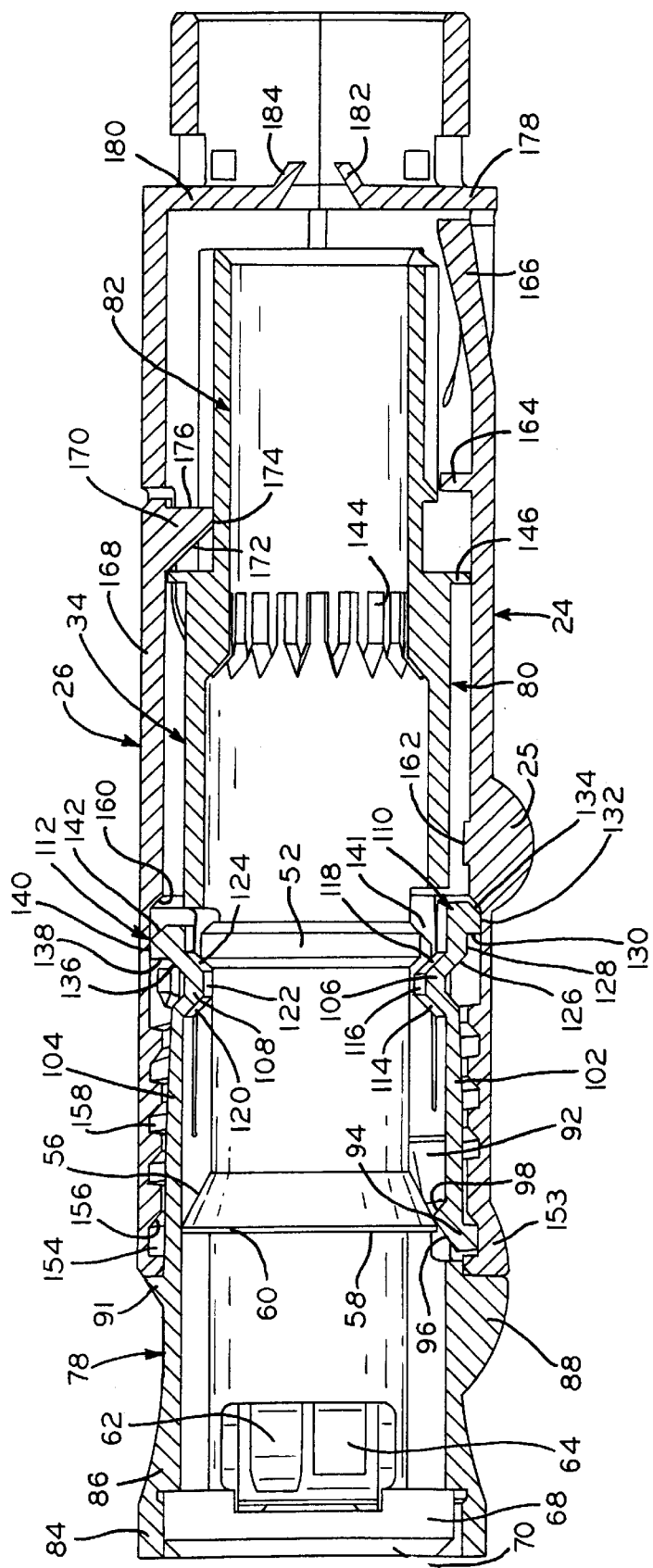
FIG. 10 is an enlarged sectional view of a portion of the medication dispensing device of FIG. 1, particularly showing the relationship among the button assembly, dial assembly, and housing while the device is at the end of dose position.
Figure 11:
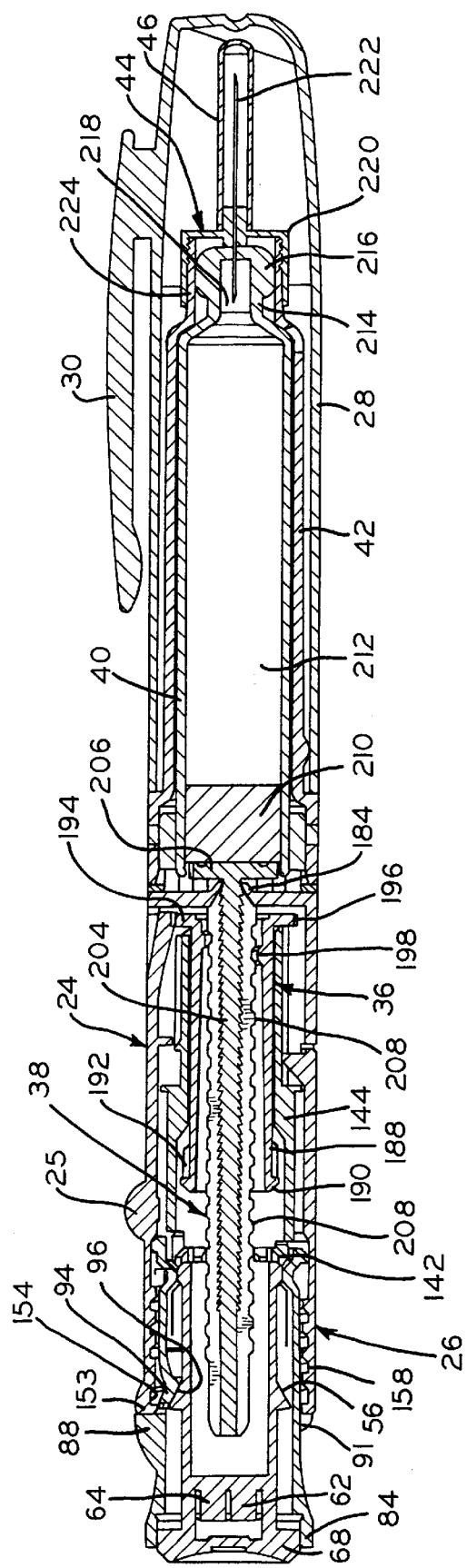
FIG. 11 is a longitudinal section dispensing device medication dispensing device of FIG. 1, particularly showing the dial assembly after it has been rotated to the zero position.

Referring to FIGS. 3 and 10, dial assembly 34 is shown in detail. Dial assembly 34 is generally cylindrical in shape and is hollow throughout its axial length. The diameter of dial assembly 34 is at a maximum at its proximal end and is at a minimum at its distal end. Referring to FIG. 3, dial assembly 34 comprises a proximal portion 78, an intermediate portion 80, and a distal portion 82. Proximal portion 78 comprises an enlarged diameter portion 84, a tapered portion 86, and an end-of-dose ring 91 extending about the circumference of proximal portion 78 as shown in FIG. 3. Ring 91 includes a bottom surface 89 (FIG. 13) that constitutes a stop surface when engaged with the rear of the housing. Ring 91 also includes an enlarged "zero-dose" protrusion 88. A generally U-shaped groove 90 (FIGS. 2, 3) is formed in proximal portion 78 to form a flexible section 92. The proximal inner surface of flexible section 92 includes a having a tapered surface 96 adapted for engagement with tapered surface 56 of disengaging device 32 and a complimentary tapered surface 98. Surfaces 96 and 98 define the inner surface of finger 94.

Proximal portion 78 of dial assembly 34 further includes a first U-shaped groove 100 (FIG. 3) and a second U-shaped groove (not shown) which form flexible legs 102, 104. Referring to FIG. 10, each leg 102, 104, includes an inwardly extending finger 106, 108, and an outwardly extending finger 110, 112, distal to the inwardly extending finger. Inwardly extending finger 106 includes proximal tapered surface 114, flat 116, and distal tapered surface 118. Likewise, finger 108 includes proximal tapered surface 120, flat 122, and distal tapered surface 124. Outwardly extending finger 110 comprises a proximal tapered surface 126, a flat 128, shoulder 130, enlarged diameter surface 132, and distal tapered surface 134. Outwardly extending finger 112 includes a proximal tapered surface 136, a shoulder 138, an enlarged diameter surface 140, and a distal tapered surface 143.

Referring to FIG. 3, a series of axial splines 142 are arranged circumferentially about the inner surface of dial assembly 34 at the area where proximal portion 78 meets intermediate portion 80. The circumferential array of splines 143 is interrupted by legs 102 and 104. In one embodiment, there are ten splines 143 positioned about the inner circumference of dial assembly 34. Referring to FIGS. 3 and 10, there is shown a plurality of splines 144 extending circumferentially about the proximal interior surface of intermediate portion 80 of dial assembly 34. Unlike splines 143, splines 144 extend 360° about the inner circumference of intermediate portion 80. In one embodiment, eighteen splines 144 are positioned such that each spline is 20 circumferential degrees apart from an adjacent spline.

Figure 7:
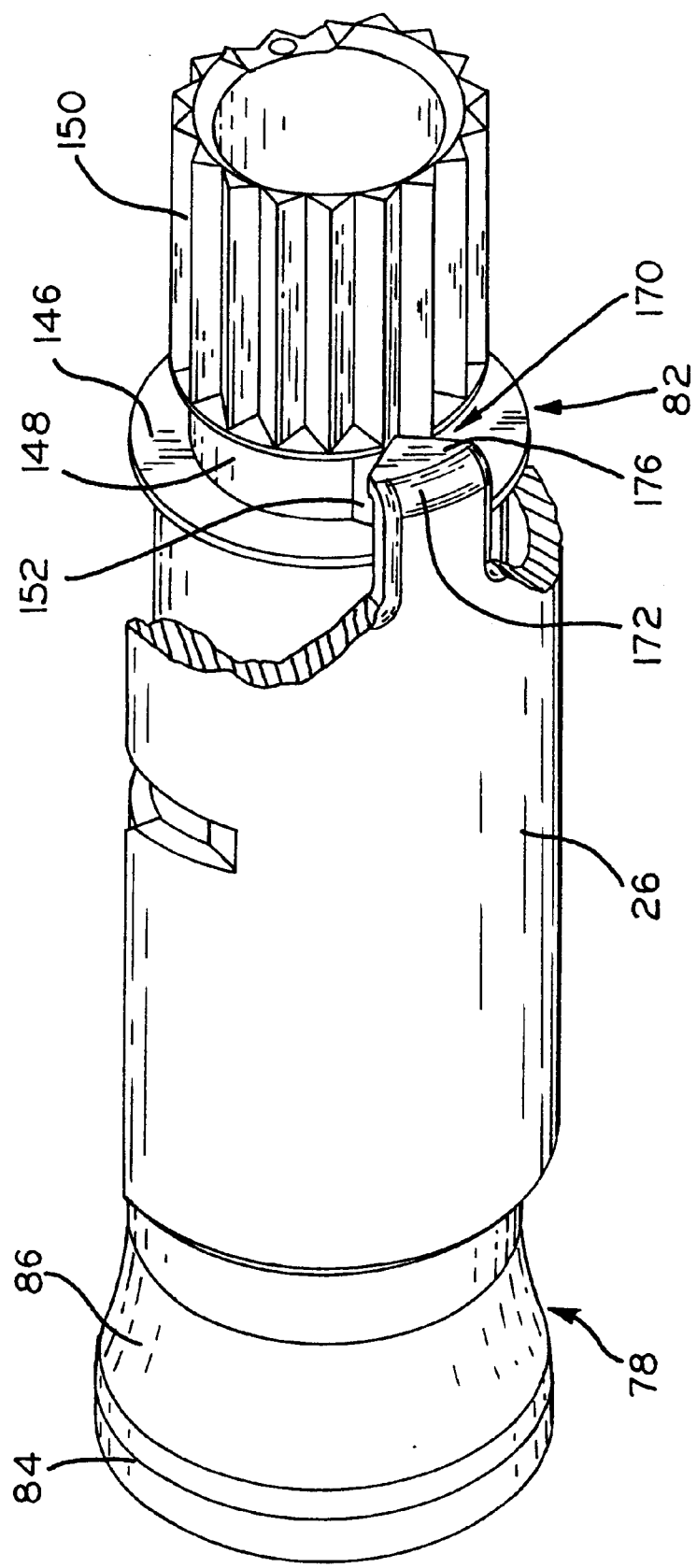
FIG. 7 is a perspective view, in partial section, of a housing part in engagement with the dial assembly, particularly showing the unit click finger in the zero position.
Figure 8:
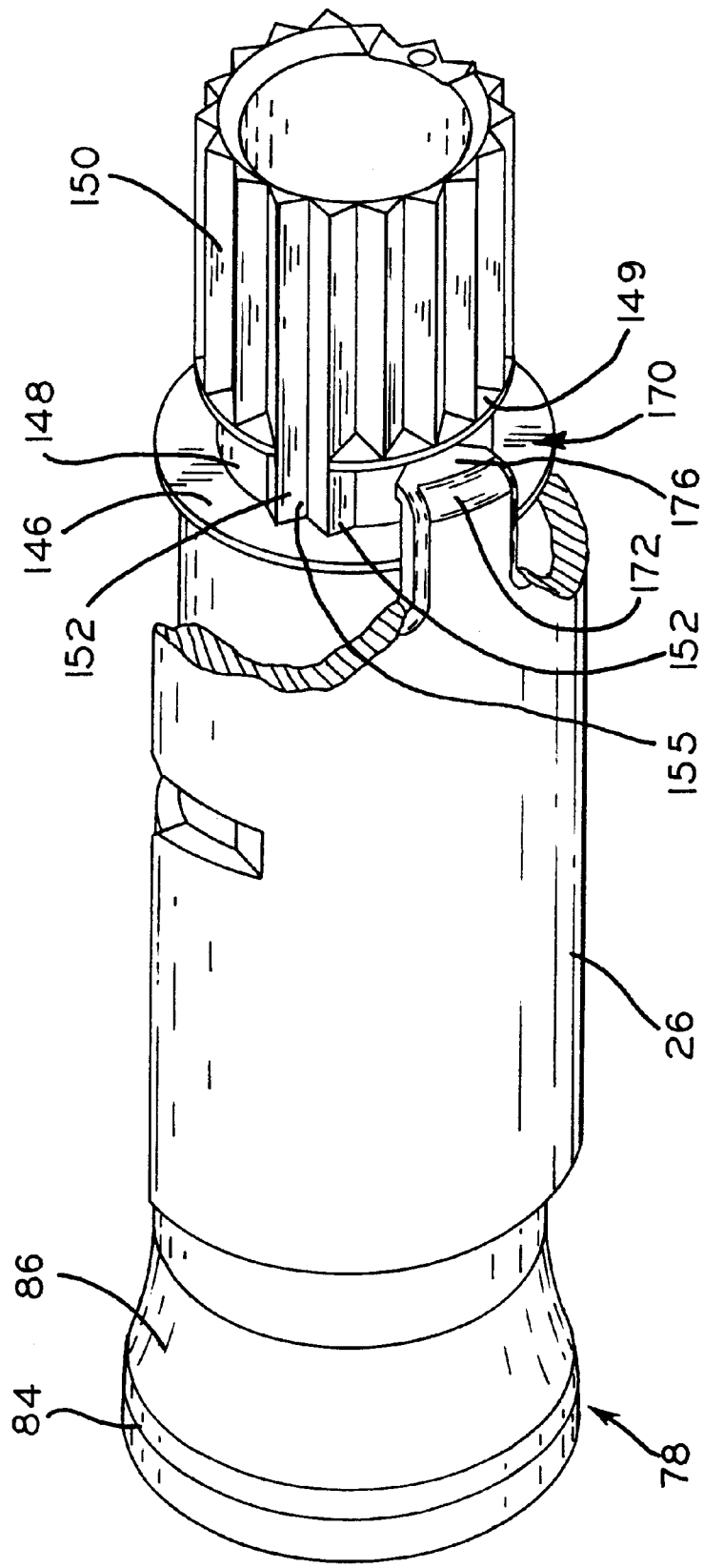
FIG. 8 is a view of FIG. 7, except that the unit click finger is behind the end-of-dose flange.
Figure 9:
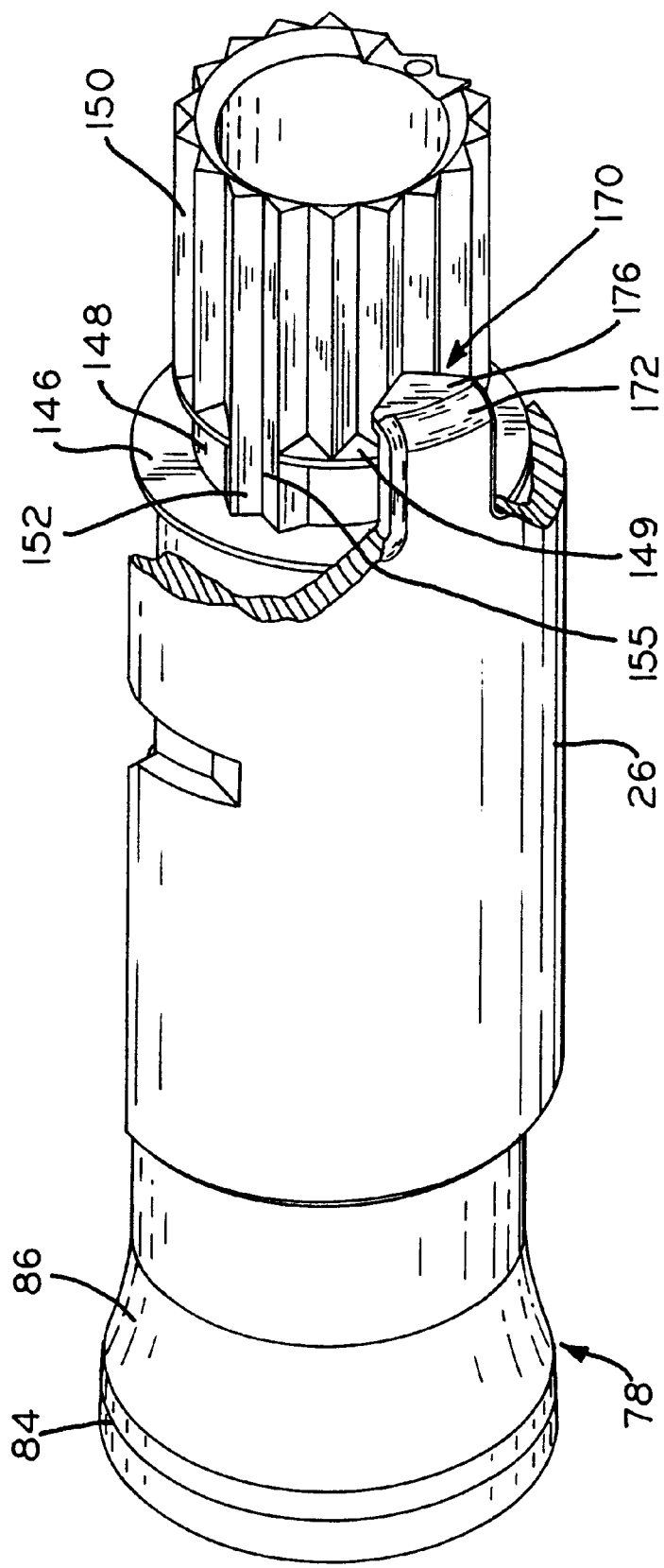
FIG. 9 is a view of FIG. 7, except that the unit click finger is shown in the dial splines during dosing.

As best shown in FIGS. 7–9, distal portion 82 of dial assembly 34 comprises a proximal flange 146, a reduced diameter portion 148, and a distal end comprising a series of elongated splines 150 extending externally about the circumference of distal portion 82. Splines 150 are in alignment with splines 144. Therefore, in one embodiment, there are eighteen splines 150, each corresponding to a respective spline 144. As shown in FIGS. 8 and 9, two of the splines 150 extend axially into reduced diameter portion 148. These extensions are indicated as splines 152.

Referring to FIG. 10, housing parts 24 and 26 form a proximal groove 154 having a tapered surface 156. Housing parts 24 and 26 further form a helical spiral groove 158 and a tapered circumferential surface 160 as shown in FIG. 10. Housing part 24 further includes a semicircular ridge 164 near the distal end thereof. Two grooves are formed at the distal portion of housing part 24 to define a flexible finger 166. Housing part 26 includes grooves formed therein to define a flexible leg 168 having an inwardly extending finger 170 at the end thereof. Finger 170 includes a proximal tapered surface 172 which terminates in a flat 174 and a vertical edge 176. Housing parts 24 and 26 include transverse ledges 178, 180, respectively, to reduce the diameter through the proximal end of the housing. Ledges 178 and 180 include flexible tangs 182, 184, respectively.

As best shown in FIGS. 11–13 and 17, medical delivery device 20 further includes nut 36 and drive stem 38. Nut 36 is generally cylindrical in shape and includes a pair of axially extending grooves 186 (FIG. 2) to form resilient proximal legs 188. Each leg 188 includes a proximal raised portion 190 and two small axially extending splines 192. The distal end of nut 36 comprises an enlarged gear-like member 194 having a plurality of teeth 196 thereon. The interior surface of the distal end of nut 36 includes a helical thread 198. Thread 198 extends about 350° about the inner surface of nut 36. A groove 200 is formed at the distal end of drive stem 138 to form legs 226, 228 (FIG. 2). Ratchet teeth 204 are located on two opposing sides of drive stem 38 and axially extend along the length of drive stem 38 from groove 200 to the distal end, which constitutes plunger engagement portion 206. Helical threads 208 extend along the axial length of drive stem 38 legs 226, 228. Drivestem 38 fits within the cylindrical opening of nut 36.

As shown in FIGS. 11–14, plunger engagement portion 206 of drive stem 38 is in engagement with piston 210 of cartridge 40. Cartridge 40 is housed within cartridge retainer 42, which is permanently secured to housing parts 24 and 26. Cartridge 40 is manufactured of glass and comprises a tube defining an inner chamber 212 which openly terminates at its distal end in a neck 214 having a cap 216 including a rubber disc 218 disposed thereover. Needle assembly 44 comprises an internally threaded base 220 and a delivery needle 222. Internally threaded base 220 is threaded onto externally threaded distal portion 224 of body 42. Needle cap 46 fits over needle 222 to prevent an inadvertent insertion of needle 222 into the patient. Cap 28 snaps onto cartridge body 42 to complete the pen-like mechanism.

In order to set a dose for injection, it is first necessary to manually zero the dial from the initial radial position of the dial resulting from the previous injection. The initial axial position of dial assembly 34, in a non-zero initial radial position with respect to housing part 26 is shown in FIG. 8. Specifically, finger 170 of housing part 26 is located in groove 148 of dial assembly 34. Groove 148 can be rotated by rotating dial assembly 34 with respect to the housing. Dial assembly 34 cannot be axially retracted due to the interference between a first element on the dose metering mechanism, i,e., ledge 149 of dial assembly 34, and a second element on the housing, i.e., vertical edge 176 of housing finger 170. Likewise, dial assembly 34 cannot be forced axially forwardly due to the interference between surface 89 on ring 91 and end surfaces 33, 35 (FIG. 4) of housing parts 24, 26, respectively. If the user mistakenly believes that it is necessary to depress disengaging device 32 to pull out the dial, finger 94 falls into groove 154 (FIG. 10), thereby creating an interference that prevents the dial from being pulled out. Upon continued rotation of dial assembly 34 with respect to housing 26, splines 152 are moved into engagement with finger 170, as shown in FIG. 7. This is the zero dose radial position of dial assembly 34. This radial zero dose position is communicated to a user in four ways. The user hears a click as splines 152 engage finger 170. The movement of finger 170 over the first spline 152 into the V-shaped recess 155 between splines 152 causes a vibration in device 20 that can be felt by the user. In addition, protrusion 88 on dial assembly 34 is in axial alignment with protrusion 153 of housing part 24, thereby providing a visual indication that the zero dose position has been reached. This is further visually communicated by the presence of a symbol in lens 25.

A series of numerals (not shown) are printed on the surface of intermediate portion 80 of dial assembly 34. These numerals are helically spaced about the circumference of portion 80 and may number from 1 to 60, in single increments, to indicate a desired dosage. The lens 25 in housing part 24 is aligned with the numbers so that the appropriate number appears in the lens upon dialing up the dosage. A raised rectangular portion lens 162 (FIG. 10) of lens 25 is located at the base of lens 25 to enhance the numerals thus making them easier to read.

Figure 6:
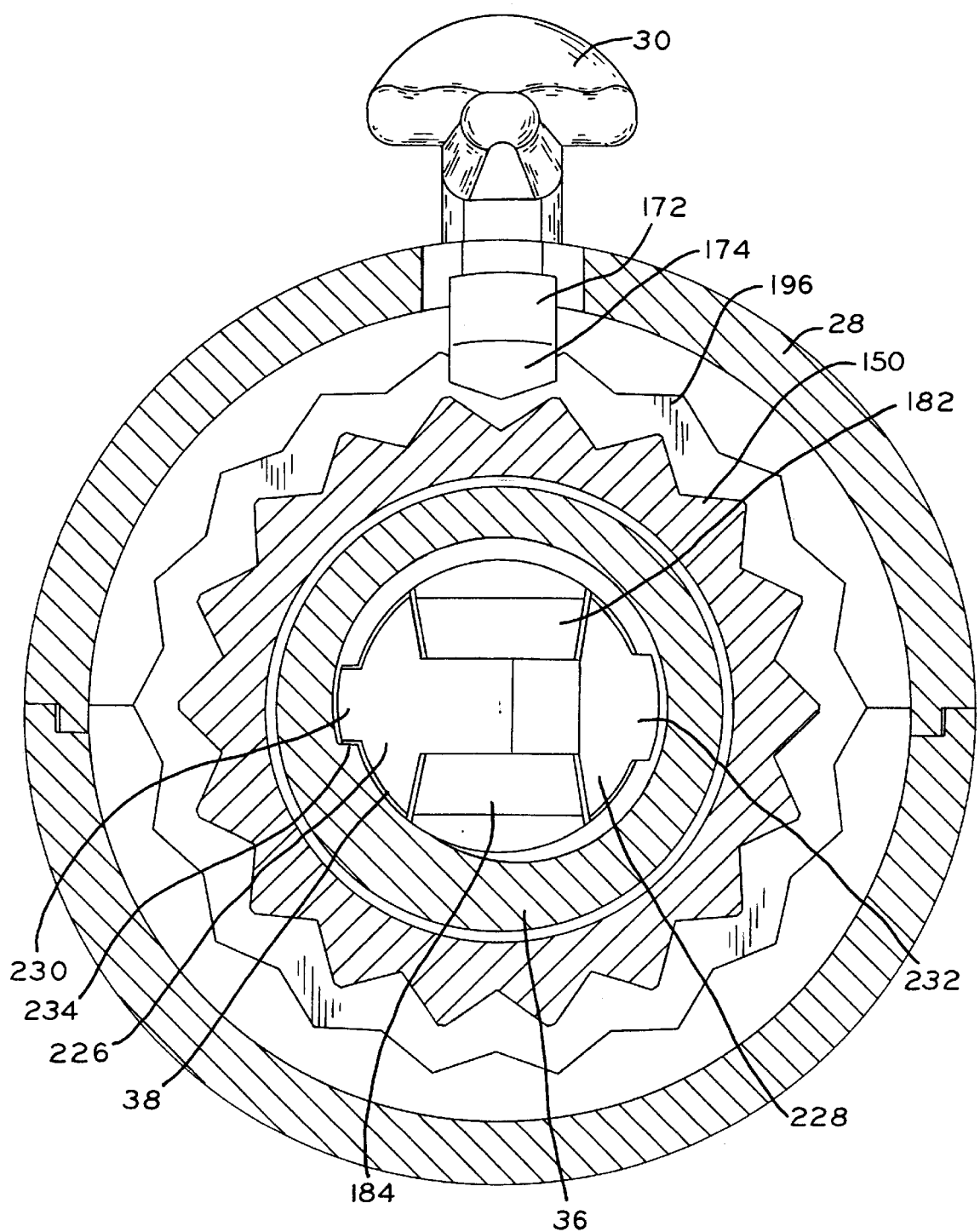
FIG. 6 is a view of FIG. 5, except that the insufficient remaining dose stop on the nut is in engagement with the stop on the leadscrew.
Figure 12:
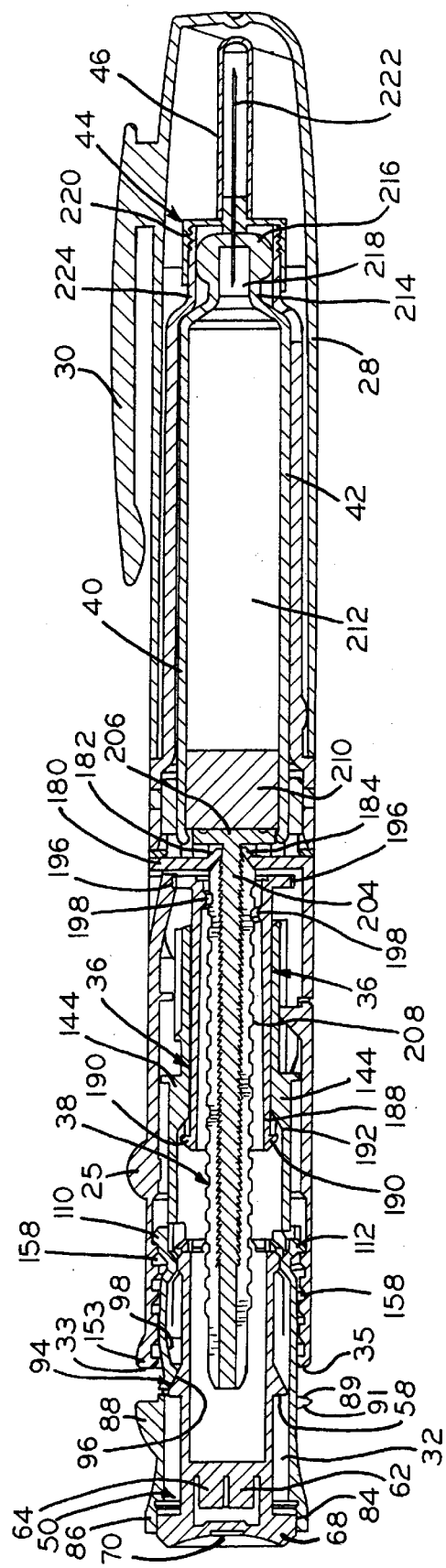
FIG. 12 is a view of FIG. 11 except that the dial assembly has been retracted so that the splines of the nut are engaged by the splines of the dial assembly.

In its zero dose position, dial assembly 34 may be axially retracted a predetermined distance, e.g. 3 to 5 mm, as illustrated in FIG. 12 to a dose setting position. As dial assembly 34 is retracted, ledge 149 is moved past housing finger 170 resulting in housing finger 170 being in engagement with splines 150. In addition, splines 144 of dial assembly 34 are moved into engagement with splines 192 of nut 36, as shown in FIG. 12. When dial assembly 34 is in a dose-setting position the clutch mechanism comprised of splines 144 and 192 is engaged and rotation of dial assembly 34 causes corresponding rotation of nut 36. Rotation of drive stem 38 is prevented by a key-keyway type of engagement between the anti-backup tangs 182 and 184 and drive stem 38. As shown in FIG. 6, tangs 182, 184 form a key, and drive stem 38 forms a keyway which comes into contact with the sides of the key.

Upon rotation of dial assembly 34 to a positive dose radial position, fingers 110, 112 move within housing groove 158 in the proximal direction to retract dial 34, thereby increasing the axial distance between stop surface 89 of ring 91 and stop surfaces 33, 35 of housing parts 24, 26. Rotation of dial assembly 34 causes rotation of nut 36 so that internal helical raised groove 198 of nut 36 rotates along external threads 208 of drive stem 38 to cause nut 36 to axially retract a corresponding axial distance. As shown in FIG. 9, rotation of dial assembly 34 causes splines 150 to move past housing finger 170. The rotation of each spline 150 past finger 170 constitutes a single unit of dosage. As each spline 150 moves past finger 170, it causes a "click" to occur, thereby providing an audible indication of each unit of dosage dialed up. In addition, a single numeral appears in lens 25 after each unit rotation indicating the current dose selected. Once a dosage has been selected, that dosage may be made larger or smaller by rotating the dial assembly in either the clockwise or counterclockwise direction.

Figure 13:
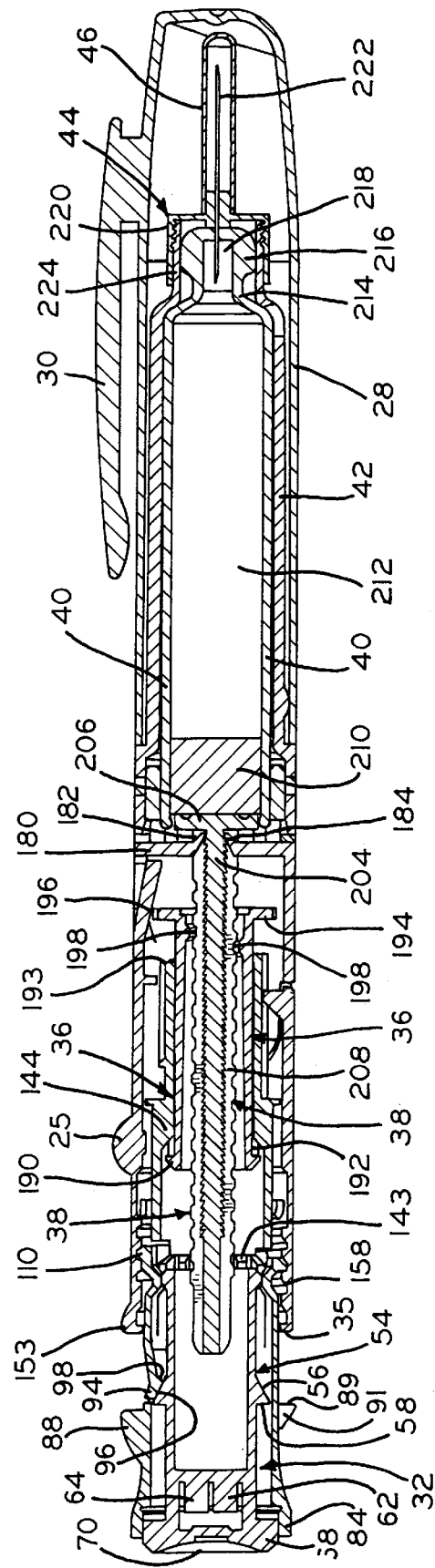
FIG. 13 is a view of FIG. 12, except that a desired dosage has been dialed up.

In one embodiment, dial assembly 34 includes eighteen splines 150 spaced 20° apart from one another. It is desired to limit the amount of dosage that can be dialed to prevent the entire contents of cartridge 40 to be delivered at once. For example, it may be desirable to limit a measured dosage to a maximum of 60 units. If the dial assembly includes eighteen splines, this would mean that a user could rotate the dial assembly for nearly 3½ rotations. As shown in FIGS. 12 and 13, as a dosage is being set, outwardly extending fingers 110 and 112 of dial assembly 34 ride in helical groove 158 of housing parts 24 and 26. Once a predetermined maximum dosage has been dialed up, e.g. 60 units, fingers 110 and 112 have reached the proximal end of the helical groove 158. Dial assembly 34 cannot be additionally rotated to further increase this maximum dosage due to an interference ledge at the end of helical groove 158. Disengaging device 32 prevents the dial assembly 34 from being inadvertently pushed forwardly during the dosing process due to the interference between fingers 110, 112 of dial assembly 34, button surface 52, and helical spiral groove 158 in housing parts 24, 26, as shown in FIG. 4. Fingers 110, 112 must be moved out of groove 158 before the dial may be moved axially forwardly. Fingers 110, 112 can be moved out of engagement with groove 158 only after fully depressing disengaging device 32, thereby moving distal surface 52 out of engagement with fingers 110, 112.

Figure 14:
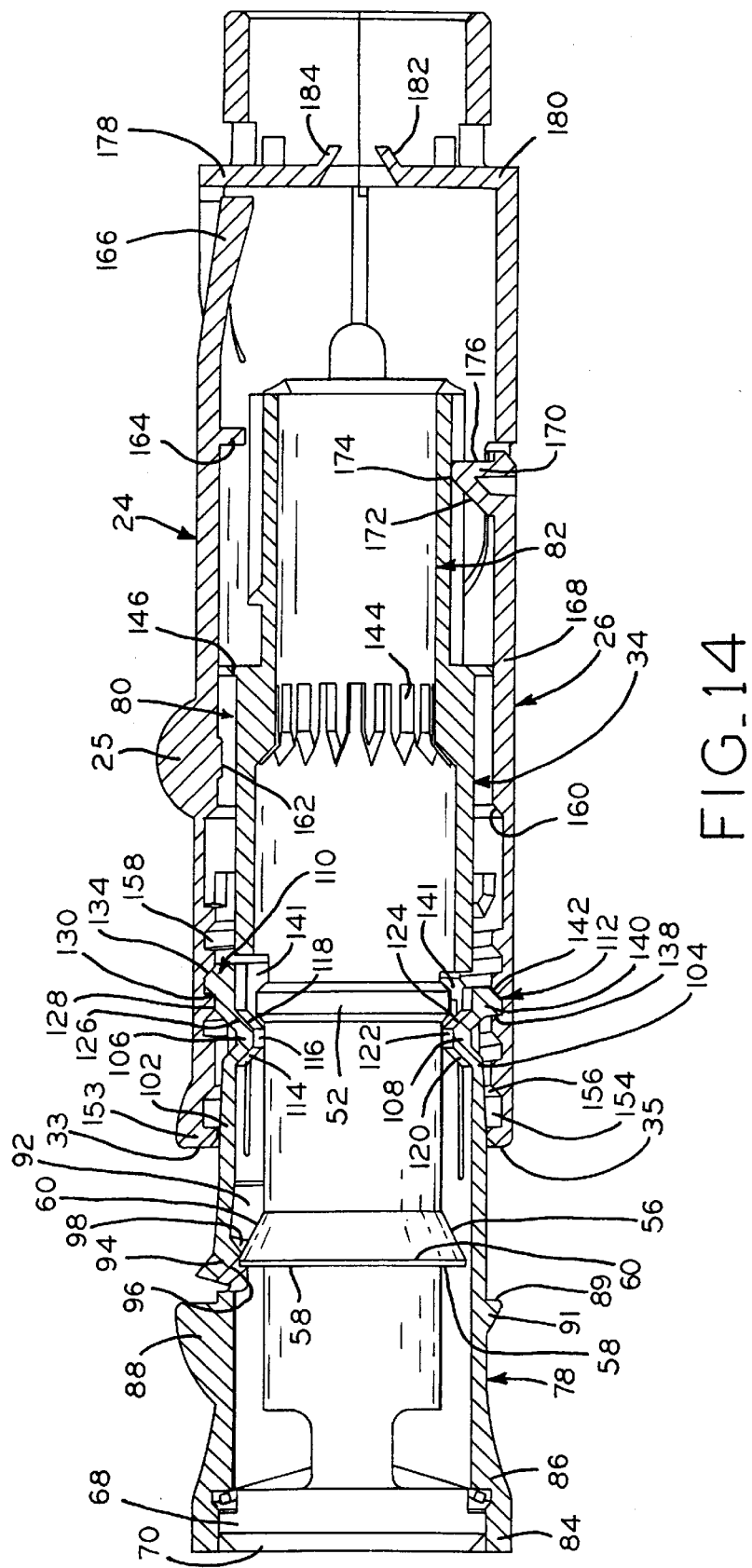
FIG. 14 is a view similar to FIG. 10, showing the dial assembly rotated 180°, and further showing the button initially depressed before dial movement takes place.
Figure 15:
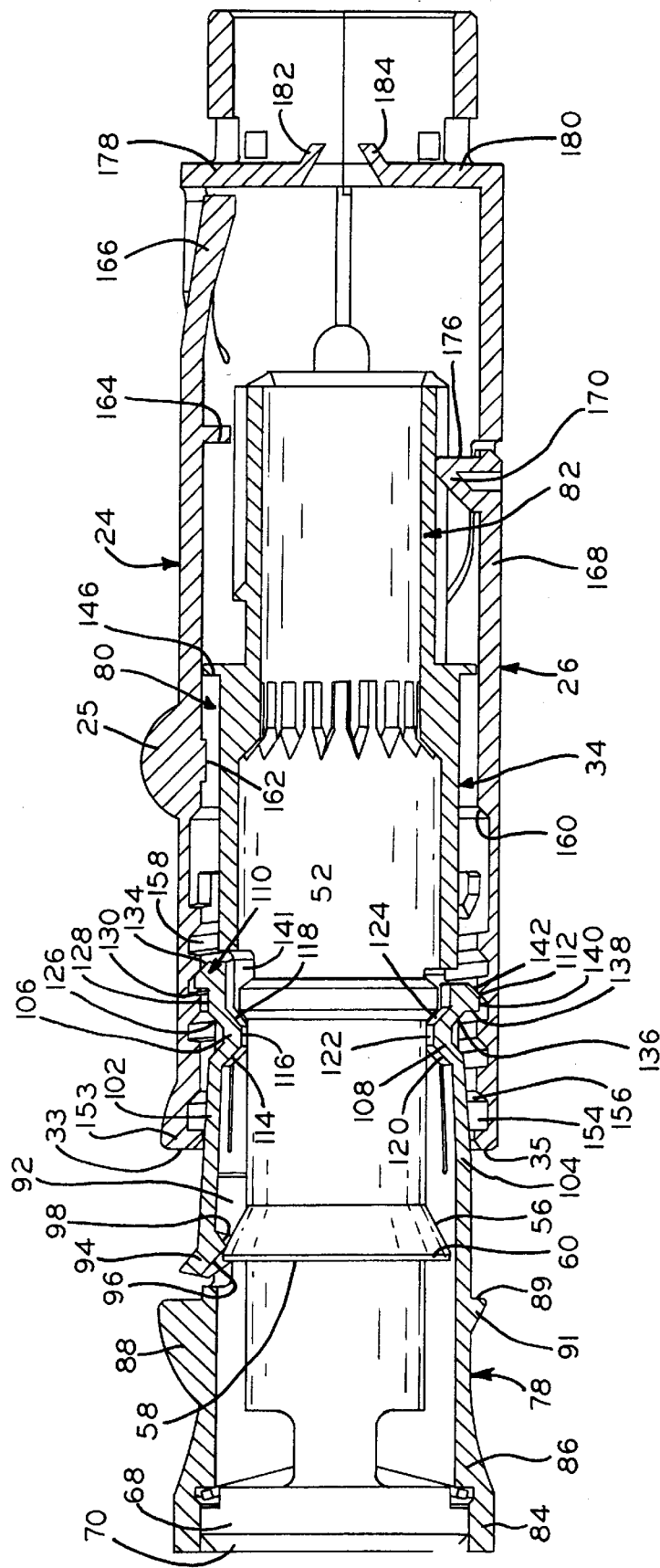
FIG. 15 is a view of FIG. 14, showing the dial having moved forward a small distance.
Figure 16:
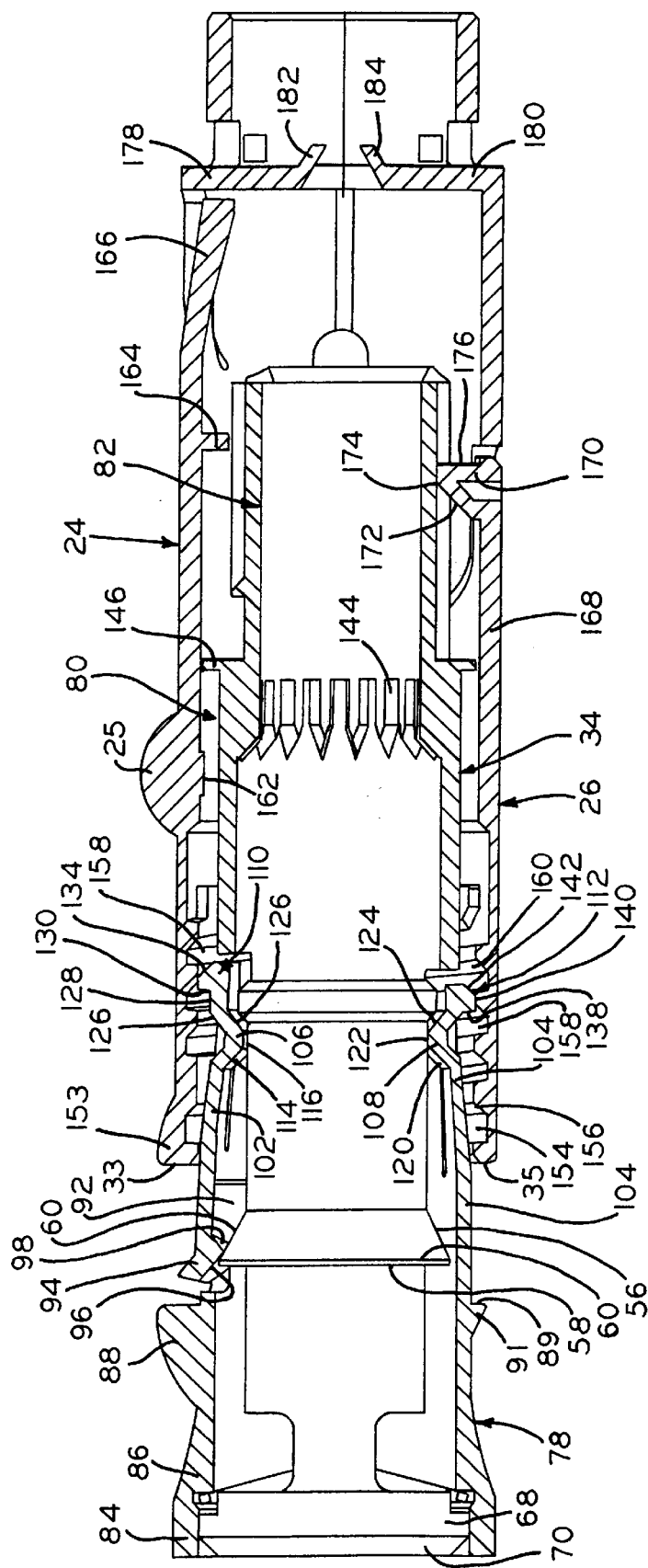
FIG. 16 is a view of FIG. 14, showing the dial having moved forward half of a thread pitch.

Once a desired dosage has been set, cap 28 is removed and needle cover 46 is removed to expose needle 222. The needle is inserted into the patient, and recessed surface 70 of disengaging device 32 is pushed. FIGS. 14–16 illustrate the initial stages of the injection process. Referring to FIG. 14, as surface 70 is pushed, disengaging device 32 moves forwardly independently of dial 34 until button distal surface 52 bottoms out against internal dial shoulder 141. Thereafter, disengaging device 32 and dial 34 are moved together. Referring to FIG. 15, as dial 34 begins to move forwardly, tapered finger surfaces 134, 142 are forced out of their respective threads 158. This causes fingers 110, 112 to flex radially inwardly. As disengaging device 32 is further pressed, fingers 110, 112 move out of respective threads 158, as shown in FIG. 16. As disengaging device 32 continues to be pressed, fingers 110, 112 move into and out of the remaining threads 158 in a like manner until dial 34 reaches its end of dose position shown in FIGS. 10 and 17. The movement of edge 95 (FIG. 4) of dial finger 94 past housing edge 157 (FIG. 4) and into groove 154 (FIG. 10) creates an audible "click" sound, thereby providing an audible confirmation that the entire dosage has been injected. Finger 94 is in close proximity to stop surfaces 89 and 33, 35. Thus, as described above, it is the non-rotational axial advancement of the dosage metering mechanism which drives the drive stem and thereby delivers the selected dosage.

As dial 34 is initially moved forwardly the clutching mechanism comprised of splines 144 and 192 decouples as splines 144 move out of engagement with splines 192 of nut 36 to rotatably disengaged dial 34 from nut 36 prior to any axial movement of nut 36. Dial 34 moves axially with respect to nut 36 until the distal end 193 (FIG. 13) of dial 34 engages nut flange 194 and moves nut 36 and drive stem 38 forwardly to deliver the set dosage of fluid.

Figure 17:
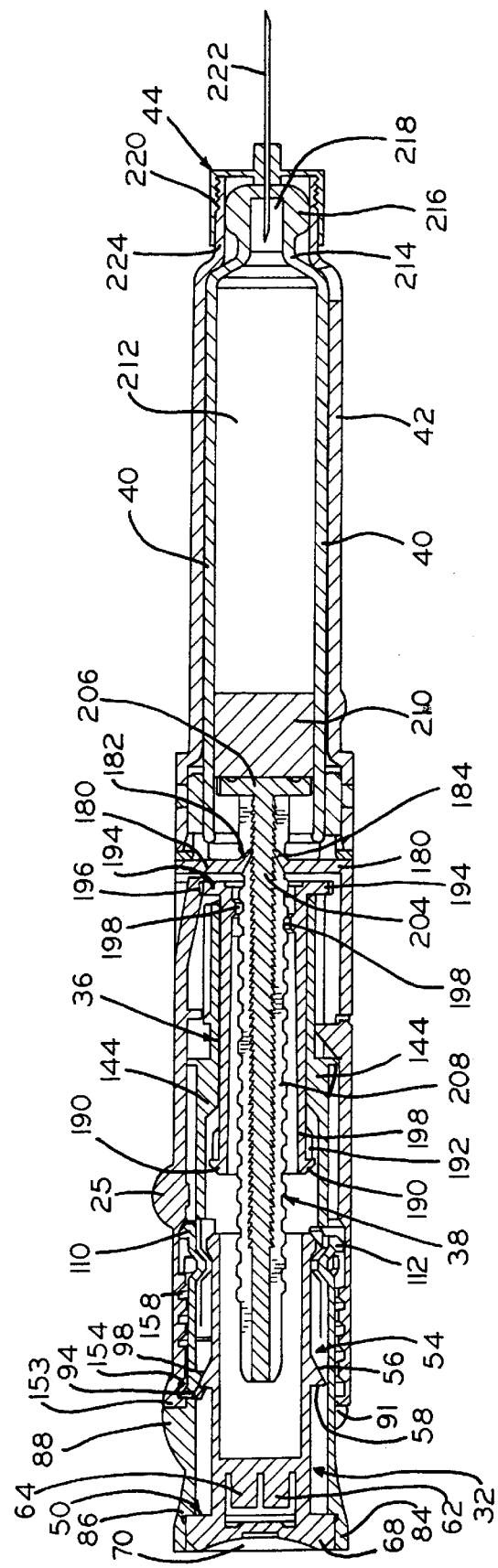
FIG. 17 is a view of FIG. 13, except that the pen is shown in its end-of-dose position.

Referring to FIGS. 10 and 17, forward movement of dial assembly 34 and nut 36 is limited by the engagement of surface 89 of ring 91 with proximal end surfaces 33, 35 of housing parts 24, 26, respectively, as shown in FIG. 14. Referring to FIG. 14, there is a small clearance, e.g. 0.4 millimeters, between nut gear or flange 194 and internal ledges 178, 180 of housing parts 24, 26, respectively. In another embodiment, the end-of-dose stop may be designed to occur between nut flange 194 and ledges 178, 180.

Movement of drive stem 38 is prevented in the proximal direction due to anti-backup tangs 182, 184 being in engagement with ratchet teeth 204. This assures that head 206 of drive stem 38 remains at all times in constant engagement with piston 210.

Once a dosage has been completed, the user releases his finger from recessed surface 70. Upon releasing pressure from surface 70, the flexible fingers or springs 62, 64 return from their stressed conditions back to their relaxed conditions, thereby automatically retracting the disengaging device 32 back to the automatic lockout position shown in FIG. 11 to prevent the dial assembly 34 from being inadvertently advanced when it is again moved to its retracted position.

Figure 5:
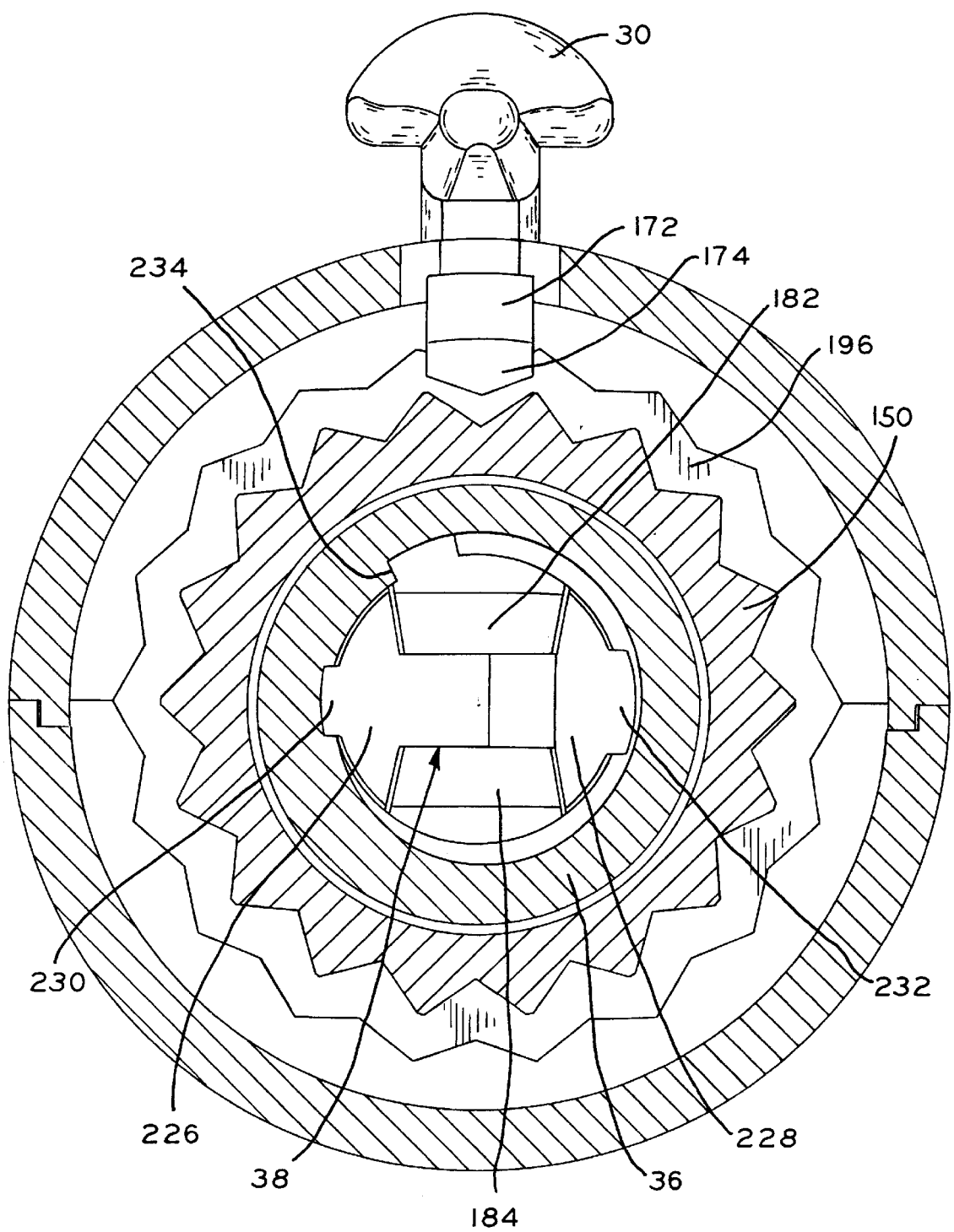
FIG. 5 is an enlarged cross sectional view of the medication dispensing device of FIG. 1, particularly showing the insufficient remaining dose stop on the nut approaching the corresponding stop on the leadscrew.

Medication device 20 further includes a mechanism to indicate to the user that there is an insufficient dosage of medication 212 remaining in cartridge 40. Referring to FIGS. 5 and 6, drive stem 38 comprises two legs 226 and 228. Leg 226 may be of a greater thickness than leg 228. Leg 226 includes an axially extending raised ledge 230 at the end of external thread 208. Leg 228 contains the end 232 of external thread 208. The internal helical thread 198 of nut 36 defines a stop surface 234 due to the fact that thread 198 extends less than 360° in circumference. As shown in FIG. 17, nut 36 moves toward legs 226, 228 of drive stem 38 as drive stem 38 moves within cartridge 40. Once nut 36 has axially moved entirely along thread 208 of drive stem 38, stop 234 approaches axial ledge 230, as shown in FIG. 5. Additional rotation of nut 36 results in stop 234 engaging ledge 230, as shown in FIG. 6. This prevents the user from dialing up a higher dosage. Nut 36 may be rotated back in the opposite direction to reduce the dosage if desired. This rotational stop mechanism provides a very accurate indication to the user of the dosage remaining in the cartridge.

It will be appreciated that the foregoing is presented by way of illustration only, and not by way of any limitation, and that various alternatives and modifications may be made to the illustrated embodiment without departing from the spirit and scope of the invention.

What is claimed is:

1. An apparatus for effecting delivery of an injectable product, comprising:

a housing;

a container secured to said housing and including an inner chamber for containing the injectable product, a piston, and an exit, the injectable product contained between said piston and said exit;

a drive stem disposed in said housing and being in engagement with said piston, wherein a length of axial movement of said drive stem with respect to said housing between a pre-injection position and a post-injection position defines a stroke length of said drive stem;

means for maintaining said drive stem in engagement with said piston by preventing axial retraction of said drive stem away from said piston;

a manually adjustable dosage metering mechanism comprising a nut rotatably engaging said drive stem and a dial assembly rotatably engageable and axially engageable with said nut, said dosage metering mechanism disposed in said housing and having an initial axial position, wherein the stroke length is zero, and a dose setting axial position corresponding to a selectively adjustable positive stroke length, said dosage metering mechanism movable between said initial axial position and said dose setting axial position by movement of said dial assembly by a user;

means coupled to said dosage metering mechanism for preventing the movement of said dosage metering mechanism from said initial axial position to said dose setting axial position until said dosage metering mechanism has been set to a radial zero dose position;

a clutching mechanism operatively disposed between said nut and said dial assembly, said clutching mechanism comprising first and second clutch surfaces respectively disposed on said nut and said dial assembly, disengagement of said clutch surfaces rotatably disengaging said nut and said dial assembly in said initial axial position and engagement of said clutch surfaces engaging said nut and said dial assembly in said dose setting axial position whereby rotation of said dial assembly in said dose setting axial position repositions said nut with respect to said drive stem; and wherein axial advancement of said dosage metering mechanism from a dose setting axial position and a positive dose radial position, towards said container to said initial position drives said drive stem from said pre-injection position to said post-injection position.

2. The apparatus of claim 1 further comprising means in said housing for causing an audible clicking noise to be made upon axially advancing said drive assembly from said pre-injection position to said post-injection position, said means for causing noise providing an audible indication to a user that a complete dosage has been delivered.

3. The apparatus of claim 1 wherein said clutching mechanism comprises a first spline disposed on said nut and a second spline disposed on said dial assembly, said splines positioned whereby said first spline is rotatably engaged with said second spline in said dose setting axial position and said splines are rotatably disengaged in said initial axial position.

4. An apparatus for effecting for effecting delivery of an injectable product, comprising:

a housing;

a container secured to said housing and including an inner chamber for containing the injectable product, a piston, and an exit, the injectable product contained between said piston and said exit;

a drive stem disposed in said housing and being in engagement with said piston, wherein a length of axial movement of said drive stem with respect to said housing between a pre-injection position and a post-injection position defines a stroke length of said drive stem;

means for maintaining said drive stem in engagement with said piston by preventing axial retraction of said drive stem away from said piston; and a manually adjustable dosage metering mechanism comprising a nut rotatably engaging said drive stem and a dial assembly rotationally engageable with said nut whereby said nut is axially repositionable with respect to said drive stem, said dosage metering mechanism disposed in said housing and having an initial axial position, wherein the stroke length is zero, and a selectively adjustable dose setting axial position corresponding to a selectively adjustable positive stroke length, said dosage metering mechanism movable between said initial axial position and said dose setting axial position by selective movement of said dial assembly by a user;

said dosage metering mechanism being movable in said initial axial position with respect to the housing between a non-dose setting radial position and a zero dose radial position, wherein said dose metering mechanism includes a first element that is in interfering relationship with a second element on said housing while said dosage metering mechanism is in said initial axial position and said non-dose setting radial position, thereby preventing movement of said dosage metering mechanism from said initial axial position to said dose setting axial position, and wherein said first element is not in interfering relationship with said second element while said dosage metering mechanism is in said zero dose radial position, thereby permitting said dosage metering mechanism to be moved from said initial axial position to said dose setting axial position.

5. An apparatus for effecting delivery of an injectable product, comprising:

a housing;

a container secured to said housing and including an inner chamber for containing the injectable product, a piston, and an exit, the injectable product contained between said piston and said exit;

a drive stem disposed in said housing and being in engagement with said piston, wherein a length of axial movement of said drive stem with respect to said housing between a pre-injection position and a post-injection position defines a stroke length of said drive stem;

means for maintaining said drive stem in engagement with said piston by preventing axial retraction of said drive stem away from said piston;

a nut rotatably and axially drivingly engaging said drive stem;

a generally cylindrical dial assembly disposed in said housing and operatively coupled with said nut; said dial assembly movable axially with respect to said housing between a dose setting axial position, wherein rotation of said dial assembly rotates said nut relative to said drive stem and adjusts the stroke length of said drive stem, and an initial axial position, wherein rotation of said dial assembly does not rotate said nut relative to said drive stem and does not change the stroke length of said drive stem;

said dial assembly being rotatable with respect to said housing in said initial axial position between a non-dose setting rotational position and a zero dose rotational position;

while said dial assembly is in said initial axial position and in said non-dose setting rotational position, a first element on said dial assembly is in interfering relationship with a second element on said housing, thereby preventing said dial assembly from being moved from said initial axial position to said dose setting axial position, and wherein, upon rotation of said dial assembly to said zero dose rotational position, said first element is moved out of interfering relationship with said second element, thereby permitting said dosage metering mechanism to be moved from said initial axial position to said dose setting axial position.

6. An apparatus for the delivery of an injectable product, comprising:

a housing;

a container mounted within said housing and including an inner chamber for containing the injectable product, a piston, and an exit, the injectable product contained between said piston and said exit, wherein movement of said piston toward the exit defines an axis of ejection of the injectable product from the container;

a manually advanceable drive stem disposed in said housing and drivingly coupled to said piston;

means for maintaining said drive stem in engagement with said piston by preventing axial retraction of said drive stem away from said piston;

a drive assembly mounted to said housing and manually axially advanceable in said housing between a dose-setting position and an injection position for manually moving said drive stem to drive said piston within said container, said drive assembly axially retractable from said injection position to said dose-setting position for selectively adjusting a stroke length of said drive stem, said drive assembly including a nut rotatably and axially drivingly engaging said drive stem and a dial assembly operatively coupled to said nut;

locking means for axially engaging said drive assembly with respect to said housing along the axis of ejection while in said dose setting position; and a disengaging device secured to at least one of said drive assembly and said housing and manually actuable to disengage said locking means whereby said drive assembly is axially disengaged from said housing to enable said drive assembly to be axially advanceable with respect to said housing to move said drive assembly from said dose setting position to said injection position.

7. The apparatus of claim 6, wherein said dial assembly comprises a generally cylindrical dial that is telescopingly disposed within said housing, and wherein said locking means is disposed on said dial and comprises a flexible finger that engages an internal groove in said housing while said drive assembly is in said dose-setting position to form an interference fit therebetween, thereby preventing non-rotational axial movement of said drive assembly with respect to said housing.

8. The apparatus of claim 7, wherein said disengaging device is generally cylindrical and is telescopingly disposed within said dial, said disengaging device including an enlarged diameter portion, said enlarged diameter portion biasing said flexible finger outwardly in a first position and when said disengaging device is advanced to a second position said enlarged diameter portion is in a non-biasing position and allows said finger to move radially inward out of engagement with said groove in said housing to enable said drive assembly to be axially advanced with respect to the housing.

9. An apparatus for effecting delivery of an injectable product, comprising:

a housing;

a container secured to said housing and including an inner chamber for containing the injectable product, a piston, and an exit, the injectable product contained between said piston and said exit;

a manually advanceable drive stem disposed in said housing and being in engagement with said piston, wherein a length of axial movement of said drive stem with respect to said housing between a dose-setting position and a post-injection position defines a stroke length of said drive stem;

means for maintaining said drive stem in engagement with said piston by preventing axial retraction of said drive stem away from said piston;

a drive assembly for manually driving said drive stem, said drive assembly engageably disposed within said housing and rotationally engaging said drive stem; said drive assembly being engageably locked from non-rotational axial movement with respect to said housing while in said dose-setting position;

said drive assembly also forming a manually adjustable dosage metering mechanism movable axially without rotation between an initial axial position, wherein the stroke length is zero, and a dose setting axial position wherein the stroke length of said drive stem is selectively adjustable by a user; and a disengaging device disposed in said housing and positioned to axially disengage said drive assembly from said housing upon initiation of an injection to enable said drive stem to move from said dose-setting position to said post-injection position.

10. An apparatus for the delivery of an injectable product, comprising:

a housing;

a container mounted within said housing and including an inner chamber for containing the injectable product, a piston, and an exit, the injectable product contained between said piston and the exit, wherein movement of said piston toward the exit defines an axis of ejection of the injectable product from the container;

a manually advanceable drive stem disposed in said housing and drivingly coupled to said piston;

means for maintaining said drive stem in engagement with said piston by preventing axial retraction of said drive stem away from said piston;

means in said housing for advancing said drive stem between a dose-setting position and an injection position, said advancing means including a nut threadedly engaging said drive stem;

locking means in said housing for axially interengaging said advancing means and said housing to lock said advancing means against axial movement along the axis of ejection while said advancing means is in said dose-setting position; and disengaging means in said housing for automatically disengaging said advancing means and said housing upon actuation thereof to unlock said advancing means and enable said drive stem to be manually advanced from said dose-setting position to said injection position.

11. An apparatus for the delivery of an injectable product, comprising:

a housing;

a container mounted within said housing and including an inner chamber for containing a quantity of injectable product which comprises multiple doses of the injectable product, a piston, and an exit, the injectable product contained between said piston and said exit;

a drive stem disposed in said housing and drivingly coupled to said piston;

a dosage metering mechanism in said housing to establish a set dosage of injectable product to be delivered, said dosage metering mechanism comprising a dial assembly rotatable with respect to said housing to establish said set dosage, said dial assembly including at least one radially flexible protrusion that is in engagement with a helical groove formed in the inner surface of said housing, said helical groove including an end, wherein rotation of said dial assembly is stopped when said at least one radially flexible protrusion comes into engagement with said end of said helical groove, thereby establishing a predetermined maximum set dosage for a single dose, said single dose being less than said quantity of injectable product containable in said inner chamber, non-rotational axial advancement of said dosage metering mechanism driving said drive stem.

12. The apparatus of claim 11 wherein a length of axial movement of said drive stem with respect to said housing between a pre-injection position and a post-injection position defines a stroke length of said drive stem, and wherein said dosage metering mechanism is movable between an initial axial position, wherein the stroke length is zero and said protrusion is disengaged from said helical groove, and a dose setting axial position wherein said protrusion is engaged with said helical groove.

13. An apparatus for effecting delivery of an injectable product, comprising:

a housing;

a container secured to said housing and including an inner chamber for containing the injectable product, a piston, and an exit, the injectable product contained between said piston and said exit;

an externally threaded drive stem disposed in said housing and drivingly coupled to said piston;

means for maintaining said drive stem in engagement with said piston by preventing axial retraction of said drive stem away from said piston;

an internally threaded nut disposed about said drive stem;

a dial assembly disposed in said housing and coupled to said nut such that rotation of said dial assembly causes rotation of said nut with respect to said drive stem to set a desired dosage of injectable product to be delivered, said dial assembly axially engageable with said nut whereby axial advancement of said dial assembly axially advances said nut;

a clutching mechanism operatively disposed between said nut and said dial assembly, said clutching mechanism comprising first and second clutch surfaces respectively disposed on said nut and said dial assembly, disengagement of said clutch surfaces rotatably disengaging said dial assembly and said nut when said dial assembly is in an initial axial position and engagement of said clutch surface rotatably engaging said dial assembly and said nut when said dial assembly is in a dose-setting axial position; and means on at least one of said nut and said drive stem for preventing rotation of said nut with respect to said drive stem as said nut engages an end of an external threaded surface of said drive stem, thereby providing an indication to a user that an insufficient dosage of injectable product remains in said container.

14. An apparatus for delivering an injectable product, said apparatus comprising:

a housing;

a container disposed within said housing, said container having an inner chamber, a piston and an exit, the injectable product contained between said piston and said exit;

an externally threaded drive stem disposed in said housing and in engagement with said piston;

a tang disposed in said housing and axially engaging said drive stem whereby said drive stem continuously engages said piston;

an internally threaded nut engaging said drive stem, rotation of said nut axially repositioning said nut on said drive stem;

a dial assembly disposed in said housing, said dial assembly being axially engageable and rotationally engageable with said nut; and a spline disposed on one of said dial assembly and said nut, said spline rotationally engaging said dial assembly with said nut while said dial assembly is in a dose-setting axial position, axial advancement of said dial assembly to an initial axial position from a dose-setting axial position axially engaging said dial assembly and said nut whereby said drive stem is axially advanceable by the axial advancement of said dial assembly, said axial advancement of said dial assembly to said initial axial position disengaging said spline whereby said dial assembly and said nut are rotationally disengaged in said initial axial position.

15. The apparatus of claim 14 wherein said housing further comprises a finger and said dial assembly further comprises a groove, said finger and said groove being axially engageable while said dial assembly is in said initial axial position, axial engagement of said groove and said finger preventing axial retraction of said dial assembly from said initial axial position to said dose setting axial position while said dial assembly is in a non-zero dose radial position, said finger axially disengaged from said groove in said initial axial position while said dial assembly is in a zero dose radial position whereby said dial assembly is axially moveable to said dose setting axial position in said zero dose radial position.

16. The apparatus of claim 14 wherein said dial assembly further comprises a finger engageable with a helical groove on said housing, engagement of said finger and said groove preventing non-rotational axial movement of said dial assembly relative to said housing, disengagement of said finger permitting non-rotational axial advancement of said dial assembly.

17. The apparatus of claim 14 wherein said spline is disposed on said nut and a second spline disposed on said dial assembly is engageable with said spline whereby engagement of said second spline with said spline rotationally engages said dial assembly with said nut.

* * * * *

UNITED STATES PATENT AND TRADEMARK OFFICE
CERTIFICATE OF CORRECTION

PATENT NO : 5,938,642
DATED : October 6, 1999
INVENTOR(S): Andrew Burroughs, et al.

It is certified that error appears in the above-identified patent and that said Letters Patent is hereby corrected as shown below:

Claim 4, Column 11, Line 39 delete "for effecting" first occurance

Claim 13, Column 15, Line 46 change "surface" to --surfaces--

Signed and Sealed this

Seventh Day of March, 2000

Attest:

Attesting Officer

Q. TODD DICKINSON

Commissioner of Patents and Trademarks